United States Patent [19]

Olivier et al.

[11] Patent Number: 5,128,482
[45] Date of Patent: Jul. 7, 1992

[54] PROCESS FOR THE PRODUCTION OF 3-1(1-AMINO-1,3-DICARBOXY-3-HYDROXY-BUT-4-YL) INDOLE

[75] Inventors: Johan Olivier; Karl Bischofberger, both of Pretoria, South Africa

[73] Assignee: Technology Finance Corporation (Proprietary) Limited, Sandton, South Africa

[21] Appl. No.: 642,804

[22] Filed: Jan. 18, 1991

[30] Foreign Application Priority Data

Jan. 19, 1990 [ZA] South Africa .................... 90/0391

[51] Int. Cl.$^5$ ................. C07D 209/18; C07D 403/06; C07D 405/06
[52] U.S. Cl. .................... 548/494; 548/502; 548/246; 548/248
[58] Field of Search ................ 548/494, 502

[56] References Cited

U.S. PATENT DOCUMENTS 3,320,282  5/1967  Wittenau et al. ................ 548/502

FOREIGN PATENT DOCUMENTS 2205834  10/1990  United Kingdom .

OTHER PUBLICATIONS

Kusumi et al. "New Synthesis-Hydroxyglutamic Acid," Bull. Chem. Soc. Jap. vol. 51(4), 1261-1262 (1978).

*Primary Examiner*—David B. Springer
*Attorney, Agent, or Firm*—Dressler, Goldsmith, Shore, Sutker & Milnamow, Ltd.

[57] ABSTRACT

The invention provides a process for the production of 3-(1-amino-1,3-dicarboxy-3-hydroxy-but-4-yl) indole and certain salts and internal condensation products thereof. An unsaturated indolyl ester is reacted with ethylchloro(hydroxyimino)acetate in the presence of triethylamine in an organic solvent to cause a 1,3-dipolar addition reaction to form a di-ester. The di-ester is saponified to form a di-acid which di-acid is then reduced to form either the product indole or a salt thereof.

9 Claims, No Drawings

PROCESS FOR THE PRODUCTION OF 3-1(1-AMINO-1,3-DICARBOXY-3-HYDROXY-BUT-4-YL) INDOLE

This invention relates to a process for the production of 3-(1-amino-1,3-dicarboxy-3-hydroxy-but-4-yl) indole, ie 4-hydroxy-4-(3-indolemethyl)-glutamic acid, whose structure can be expressed by the

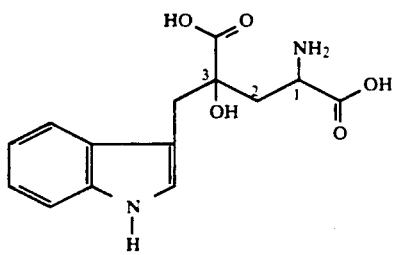

(I)

which indole has, by virtue of the two asymmetric carbon atoms located respectively at the 1 and 3 positions, four stereoisomers. More particularly the invention relates to a process suitable for producing the naturally occurring SS diastereomer, salts thereof at the 1 and/or 3 positions, and certain internal condensation products thereof.

According to the invention there is provided a process for the production of said indole according to formula (I) and the salts thereof at the and/or 3 positions and internal condensation products thereof, which process comprises the steps of:

reacting an unsaturated carboxylate starting material of the formula (II), ie

(II)

(in which $R_o$ is a suitable leaving group or a suitable removable activating group and $R_1$ is H or an alkyl, aryl or aralkyl group, which group may be substituted)

with a substituted alkyl hydroxyimino carboxylate starting material of the formula (III), ie

(III)

(In which X is a radical which leads to the formation of nitrile oxide in the presence of a base when said compound of formula (III) is dissolved in an organic solvent, and $R_2$ is H or an alkyl, aryl or aralkyl group, which group may be substituted)

under reaction conditions which cause a 1,3-dipolar addition reaction to take place between then, to form a di-ester of the formula (IV), ie

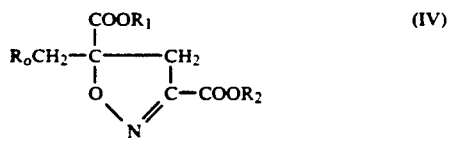

(IV)

saponifying the di-ester of formula (IV) to form a di-acid of formula (V), ie

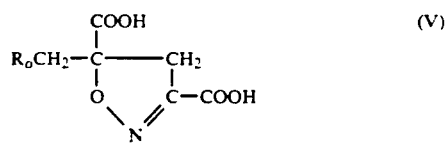

(V)

reducing the di-acid of formula (V) to yield a compound of formula (VI), ie

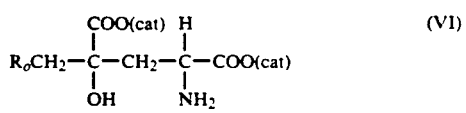

(VI)

(In which (cat) is H or a monovalent cation); and if necessary, replacing $R_o$ with an indole group.

Conveniently, the unsaturated carboxylate starting material of formula (II) is an unsaturated indolyl ester in which $R_o$ is indole, in which case replacing $R_o$ with an indole group after the reducing of the di-acid of formula (V) will not be necessary.

In the unsaturated carboxylate starting material of formula (II), $R_1$ may be a short-chain alkyl group having <5 carbon atoms, eg ethyl or, particularly, methyl.

The indolyl ester starting material of formula (II) can be made by a preliminary step whereby indole is reacted in a suitable solvent in the presence of a suitable alkyl magnesium halide Grignard reagent such as ethyl magnesium bromide with a suitable alkyl halomethacrylate such as methyl bromomethacrylate. Suitable solvents include ether, ether/benzene blends, and tetrahydrofuran (THF). In particular, the process of the present invention may include the preliminary step of producing the unsaturated indolyl ester starting material of formula (II) in which $R_1$ is methyl, by reacting indole with methyl bromomethacrylate in the presence of ethyl magnesium bromide, according to the reaction

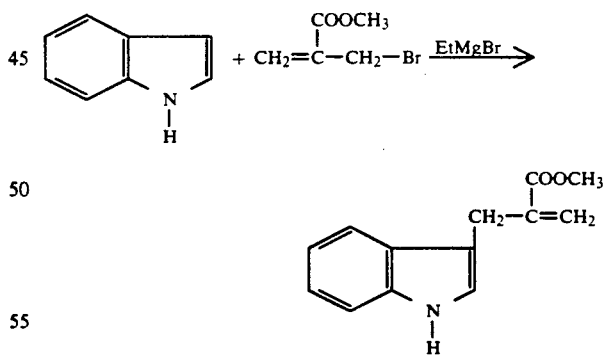

Suitable yields of up to 60–65% can be obtained at temperatures of −30° to 30° C., eg −25° to −15° C., using THF as the solvent and with or without reverse addition of the Grignard reagent. Routine experimentation should be employed, taking economic considerations into account, to establish acceptable or optimal reagents, solvents and reaction parameters.

Methyl bromomethacrylate can be prepared according to the malonic ester route (Ferris, J. Org. Chem, 20, 780 (1955)) but is more easily prepared by the so-called Bayes-Hillman route (Drews, Synt. Comm., 17(3), 291

(1987)), ie reacting paraformaldehyde with methyl acrylate according to the reaction

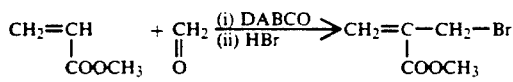

wherein the DABCO (ie 1,4-diazabicyclo(2.2.2)octane)-catalysed coupling reaction between the paraformaldehyde and methyl acrylate proceeds without difficulty, but the bromination step should be effected preferably by bubbling HBr through the reaction mixture, taking care to avoid excessive bromination which leads to the production of

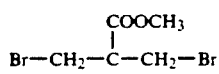

The reaction of the starting materials of formulae (II) and (III) with each other may be carried out in solution in an organic solvent in the presence of an amine, preferably an alkyl-substituted amine such as a trialkyl amine, in particular triethylamine.

In the substituted alkyl hydroxyimino carboxylate starting material of formula (III) in turn, the radical X may be a halogen radical such as a chlorine radical, and the alkyl group $R_2$ may be a short-chain alkyl group having <5 carbon atoms, being eg methyl or, particularly, ethyl. The substituted alkyl hydroxyimino carboxylate starting material of formula (III) is thus preferably ethyl chloro(hydroxyimino) acetate.

The reaction between the starting materials (II) and (III) may take place in a suitable organic solvent, such as chloroform, which is preferably dry, at ambient temperatures, with stirring, followed after completion of the reaction by separation of the organic phase comprising the di-ester of formula (IV) and drying thereof, eg with anhydrous $MgSO_4$ and concentration under vacuum.

Saponifying the concentrated di-ester of formula (IV) may be by means of a suitable metal hydroxide, eg an alkaline earth metal hydroxide or an alkali metal hydroxide such as potassium hydroxide (KOH), which may be dissolved in a suitable solvent, eg an alcohol such as ethanol, followed preferably by desalting eg with a suitable cation exchange resin and concentration under vacuum to provide the di-acid of formula (V) as a solid.

The reducing of the di-acid of formula (V) may be by means of a suitable reducing agent such as a solution of sodium in isopropanol, sodium cyanoborohydride or an amalgam such as sodium amalgam (NaHg). Reducing by means of NaHg can be effected with the di-acid of formula (V) dissolved in water/ethanol, by addition of the NaHg to the solution at ambient temperatures. Accordingly, reducing the di-acid of formula (V) may be such as to yield a compound according to formula (VI) which is a salt in which (cat) is Na. This sodium salt of formula (VI) can be converted to the indole of formula (I), as a mixture of four diastereomers, by elution, eg with dilute aqueous ammonia solution, a 5% by mass solution being suitable, by cation exchange using a suitable cation exchange resin.

The indole so produced is a mixture of four diastereomers. The process may include separating the SS and RR diastereomers from the mixture by dissolving it in an aqueous solvent and adding an acid, eg a mineral acid, to the solution so formed, to precipitate said SS and RR diastereomers. This separation can thus conveniently be effected by precipitation from aqueous solution with hydrochloric acid, followed in turn by filtration, dissolving in an aqueous sodium hydroxide solution, cation exchange chromatography, elution with dilute aqueous ammonia solution and freeze drying, to obtain a mixture of two enantiomers, ie the naturally occurring SS diastereomer and the RR diastereomer. These diastereomers can be separated eg by means of a chiral high pressure liquid chromatography column; or enzymatically, eg using de-aminase enzyme to destroy the RR isomer, or by making a chloroacetyl derivative of the diastereomers which can then be resolved using acylase-1 enzyme.

As indicated above, the sodium salt of formula (VI) can be converted to the indole of formula (I), eg by means of cation exchange using a suitable cation exchange resin by elution with ammonia. This sodium salt, and the indole itself, can easily be used to produce other salts, such as the potassium, ammonium, alkylammonium, calcium and magnesium salts, by cation exchange, using eg a suitable 'Biorad' cation exchange resin available from Bio-Rad Laboratories, Richmond, Calif., U.S.A.

Furthermore, internal condensation products can be obtained of the indole, which are the lactone of formula (VII)

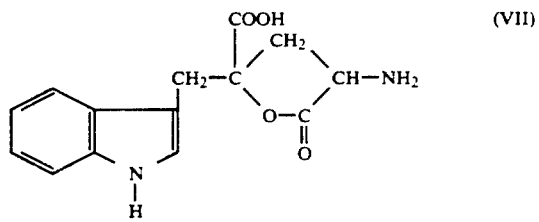

and the lactam of formula (VIII)

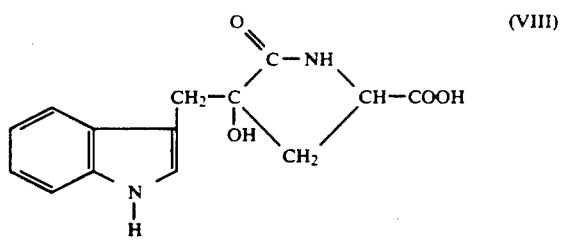

The lactone of formula (VII) can form reversibly, depending on the pH, in aqueous solution, from the indole of formula (I) by condensation, and the condensation can be reversed, almost completely, by appropriately altering the pH, to form said indole.

The lactam of formula (VIII) can be formed by preparing the ethyl ester on the 3 position, followed by spontaneous actamization.

The invention extends, accordingly, to the indole of formula I), and to the salts thereof at the 1 and/or 3 positions, and to the actone of formula (VII) and the lactam of formula (VIII), whenever reduced by the process of the present invention.

The invention will now be described, in non-limiting fashion, with reference to the following illustrative Examples.

EXAMPLE 1

Ethyl magnesium bromide was prepared from magnesium turnings (292 mg, 12 mmol) in dry ether (4 ml) and ethylbromide (1,308 g, 12 mmol) in dry ether (1,3 ml). A solution of indole (1,17 g, 10 mmol) in dry benzene (2 ml) was added slowly to the ethyl magnesium bromide solution with stirring which was continued for 20 minutes at room temperature. Methyl bromomethacrylate (1,969 g, mmol) in dry benzene (1,5 ml) was then added slowly at 0° C., a mild exothermic reaction taking place. The mixture was stirred for 1 hour at room temperature, quenched with water, and extracted with ethyl acetate. The ethyl acetate was dried with anhydrous $MgSO_4$ and then concentrated under vacuum to give a brown syrup (2,5 g). Chromatography on silica and elution with toluene:ethyl acetate (19:1) produced some unreacted indole (160 mg, 13,7 %) followed by the desired exomethylene compound (indolyl ester according to formula (II) in which $R_1$ is methyl) as a light brown syrup (1,00 g, 46,5%) which solidified on standing.

A solution of ethyl chloro(hydroxyimino) acetate (91 mg, 0,6 mmol) in dry chloroform (1 ml) was added dropwise to a solution of the unprotected indolylester according to formula (II) (65 mg, 0,3 mmol) with triethylamine (101 mg, 1,0 mmol) in dry chloroform (1 ml) over a period of 4 hours at room temperature. The mixture was stirred overnight. The reaction mixture was washed with water. The organic phase was separated from the aqueous phase, dried with anhydrous $MgSO_4$ and concentrated under vacuum to produce a yellow syrup. Chromatrography on silica and elution with toluene:ethyl acetate (17:3) produced the pure cycloaddition di-ester product (formula (IV)) in which $R_1$ is methyl and $R_2$ is ethyl) (96 to 97,0%) as a pale yellow oil.

A solution of said di-ester (218 mg, 0,66 mmol) and KOH 85% (99 mg, 1,50 mmol) in 80% EtOH (ie an ethanol/water mixture comprising 80% by mass etanol) (5 ml) was stirred at room temperature for 1 hour to saponify the di-ester. The mixture was desalted by passing it through a cation exchange resin (Biorad, AG 50W-X8, 3 ml) and rinsing the resin with a few ml, of 80% EtOH. Concentration of the solution under vacuum provided the di-acid according to formula (V) in which $R_1$ is methyl and Rz is ethyl, as a yellow crystalline product (164 mg, 96,2%).

A solution of said di-acid (42 mg; 0,146 mmol) in water (I ml) was treated with NaHg 5% (1050 mg, 2,28 mmol Na) at room temperature for 5 hours, to produce the sodium salt of formula (VI) at the 1 and 3 positions of the indole of formula (I). Thin layer chromatography on silica, and elution with n-BuOH-AcOH-$H_2$) (3:2:1) showed one major spot with the same rf as the naturally occurring SS isomer of the indole of formula (I). The reaction mixture was separated from the residual mercury by gravity and filtration, and was then chromatographed on cation exchange BioRad, AG 50W-X8 100–200 mesh (5 ml). Elution with aqueous ammonia (5%, 20 ml) produced the indole of formula (I) (4 diastereomers) as a pale yellow glass. This product was then freeze dried to give a foamy product (40 mg, 93,9%).

The mixture of four isomers of product (40 mg) was dissolved in 1 ml water and 1 molar equivalent of 1 Normal aqueous HCl was added slowly thereto, to produce a white precipitate which was filtered. This precipitate was dissolved in 1 molar equivalent of 1 Normal aqueous NaOH and chromatographed on cation exchange BioRad, AG 50W-X8 100–200 mesh (5 ml). Elution with aqueous ammonia (5%, 10 ml) provided the product as a purified 50:50 mixture of 2 enantiomers (the SS diastereomer (naturally occurring) and the RR diastereomer), which mixture has a sweet taste. This mixture was freeze dried to produce 25 mg of product.

EXAMPLE 2

Example 1 was repeated, except that, initially, ethyl magnesium bromide was prepared in the same fashion as Example 1 but using tetrahydrofuran (THF) as solvent instead of the dry ether of Example 1. Similarly, the methyl bromomethacrylate was added dissolved in THF instead of dry benzene, and the addition took place at $-20°$ C., dropwise during a period of <3 minutes. After stirring and quenching as in Example 1, THF was distilled off under vacuum and the aqueous residue was extracted with ethyl acetate, dried with anhydrous $MgSO_4$ and concentrated under vacuum to give a yellow syrup. Chromotography on silica (130 g) and elution with toluene-ethyl acetate (19:1) gave some unreacted indole (230 mg, 19,6%) followed by the indole ester of formula (II) (1,36 g, 63,2%) as pale brown crystals.

In Example 2 the methyl bromomethacrylate was prepared by stirring together methyl acrylate (103 g, 1,2 mol), paraformaldehyde (54,2 g, 1,8 mol) and DABCO (6,72 g, 60 mmol) in a 250 ml autoclave at 95° C. for 4 hours. Cooling gave a crude alcohol-ether mixture (150 g) which was dissolved in 48% aqueous HBr (240 g) and saturated with HBr bubbled therethrough after cooling to about 35° C. with iced water, followed by stirring at 35° C. for 2 hours. The reaction, mixture was then quenched with iced water and extracted with hexane. The hexane, which separated as a layer, was washed 6 times with water, dried with anhydrous $MgSO_4$ and extracted under vacuum (20 mm Hg). The crude methyl bromomethacrylate so obtained was distilled under high vacuum (22° C./0,2 mm Hg) using a receiving flask cooled in a dry-ice/acetone bath to obtain a purified methyl bromomethacrylate product (52 g, 45%).

Thereafter Example 1 was followed, the above steps in Example 2 being an improvement over the corresponding steps in Example 1, particularly as regards the yields obtained of indole ester of formula (II) and methyl bromomethacrylate.

It will be appreciated that because of the high yield which are in principle obtainable, as shown by the Examples, the method of the invention, particularly as described with reference to the Examples, presents a substantial improvement over the known methods of production of the indole of formula (I) and its salts and internal condensation products.

It will be appreciated further that there are no doubt many variations in detail possible with a method of preparing the indole of formula (I) and related compounds as herein described without departing from the spirit and/or scope of this disclosure.

What is claimed is:

1. A process for the production of 3-(1-amino-1,3-dicarboxy-3-hydroxy-but-4-yl) indole according to the formula (I):

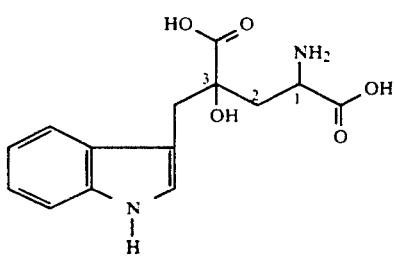 (I)

and pharmaceutically acceptable salts thereof at the 1 and/or 3 positions and the internal condensation products thereof, which are the lactone of formula (VIII):

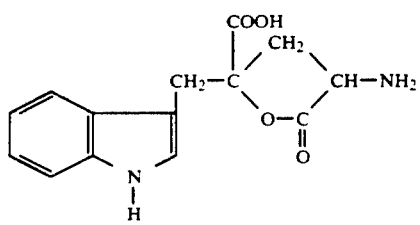 (VII)

and the lactam of formula (VIII):

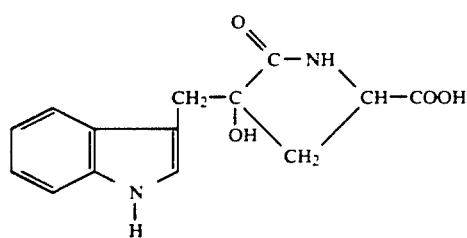 (VIII)

which process comprises the steps of:
reacting an unsaturated indolyl carboxylate starting material of the formula (II)

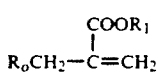 (II)

(in which $R_o$ is an indole group and $R_1$ is H or an alkyl, aryl or aralkyl group, which $R_1$ group may be substituted) with a substituted alkyl hydroxyimino carboxylate starting material of the formula (III)

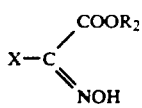 (III)

(in which X is a halogen radical and $R_2$ is H or an alkyl, aryl or aralkyl group, which $R_2$ group may be substituted)
in solution in an organic solvent in the presence of a base to cause a 1,3-polar addition reaction to take place between then to form a di-ester of the formula (IV)

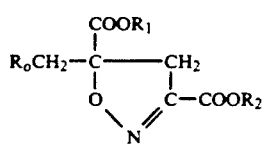 (IV)

saponifying the di-ester of formula (IV) by means of a basic reagent to form a di-acid of the formula (V)

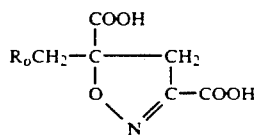 (V)

and;
chemically reducing the di-acid of formula (V) to yield a compound of formula (VI)

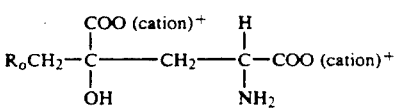 (VI)

(in which (cation)+ is H or a pharmaceutically acceptable monovalent cation).

2. A process as claimed in claim 1, in which the unsaturated indolyl carboxylate starting material of formula (II) is one in which $R_1$ is methyl.

3. A process as claimed in claim 2, which includes the preliminary step of producing the unsaturated indolyl ester starting material of formula (II) in which $R_1$ is methyl by reacting indole with methyl bromomethacrylate in the presence of ethyl magnesium bromide, according to the reaction

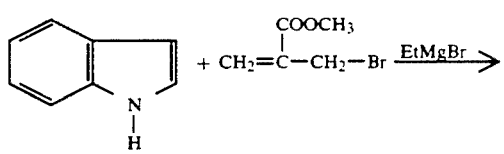

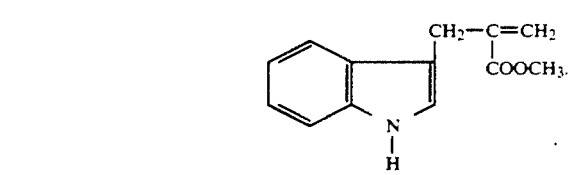

4. A process as claimed in claim 1, in which the base, in whose presence the reaction of the starting materials of formulae (II) and (III) with each other is carried out, is triethylamine.

5. A process as claimed in claim 1, in which the substituted alkyl hydroxyimino carboxylate starting material of formula (III) is ethyl chloro(hydroxyimino) acetate.

6. A process as claimed in claim 1, in which the saponification of the di-ester of formula (IV) is effected by means of potassium hydroxide.

7. A process as claimed in claim 1, in which reducing the di-acid of formula (V) is such as to yield a compound according to the formula (VI) in which (cation)+ is Na.

8. A process as claimed in claim 7, which includes the step of converting the sodium salt of formula (VI) to the indole of formula (I), as a mixture of four diastereomers, by cation exchange.

9. A process as claimed in claim 8, which includes separating the SS and RR diastereomers of said indole of formula (I) from the remaining diastereomers thereof, by dissolving said indole in an aqueous solvent and adding an acid to the solution so formed to precipitate said SS and RR diastereomers.

* * * * *

UNITED STATES PATENT AND TRADEMARK OFFICE
CERTIFICATE OF CORRECTION

PATENT NO. : 5,128,482

DATED : July 7, 1992

INVENTOR(S) : Johan Olivier and Karl Bischofberger

It is certified that error appears in the above-identified patent and that said Letters Patent is hereby corrected as shown below:

Column 4, line 59, "ethyl" should be --methyl--.

Column 5, lines 46-47, delete "in which $R_1$ is methyl and $R_2$ is ethyl".

Column 6, line 52, "high yield" should be --high yields--.

Signed and Sealed this

Sixth Day of July, 1993

Attest:

MICHAEL K. KIRK

*Attesting Officer*    *Acting Commissioner of Patents and Trademarks*

UNITED STATES PATENT AND TRADEMARK OFFICE
CERTIFICATE OF CORRECTION

PATENT NO. : 5,128,482

DATED : July 7, 1992

INVENTOR(S) : Johan Olivier and Karl Bischofberger

It is certified that error appears in the above-identified patent and that said Letters Patent is hereby corrected as shown below:

Column 1, line 9, after "the" insert --formula (I), ie--;
        line 59, "then" should be --them--.

Column 4, line 60, "actamization" should be --lactamization--.

Column 5, line 10, before "mmol" insert --11--.

Column 7, line 14, "(VIII)" should be --(VII)--;
        line 59, "then" should be --them--.

Signed and Sealed this

Seventeenth Day of August, 1993

Attest:

BRUCE LEHMAN

Attesting Officer    Commissioner of Patents and Trademarks